(12) United States Patent
Zheng et al.

(10) Patent No.: US 9,725,517 B2
(45) Date of Patent: Aug. 8, 2017

(54) HUMANIZED MONOCLONAL ANTIBODIES AGAINST THE EXTRACELLULAR DOMAIN OF HUMAN DEATH RECEPTOR 5

(71) Applicant: Institute of Basic Medical Sciences, Chinese Academy of Medical Sciences, Beijing (CN)

(72) Inventors: Dexian Zheng, Beijing (CN); Yuhe Qiu, Beijing (CN); Yanxin Liu, Beijing (CN)

(73) Assignee: Institute of Basic Medical Sciences, Chinese Academy of Medical Sciences, Beijing (CN)

( * ) Notice: Subject to any disclaimer, the term of this patent is extended or adjusted under 35 U.S.C. 154(b) by 8 days.

(21) Appl. No.: 14/435,684

(22) PCT Filed: Oct. 26, 2012

(86) PCT No.: PCT/CN2012/083627
§ 371 (c)(1),
(2) Date: Apr. 14, 2015

(87) PCT Pub. No.: WO2014/063368
PCT Pub. Date: May 1, 2014

(65) Prior Publication Data
US 2015/0353638 A1    Dec. 10, 2015

(51) Int. Cl.
*C07K 16/28* (2006.01)
*A61K 39/395* (2006.01)
(Continued)

(52) U.S. Cl.
CPC ........ *C07K 16/2878* (2013.01); *A61K 31/704* (2013.01); *A61K 39/3955* (2013.01);
(Continued)

(58) Field of Classification Search
None
See application file for complete search history.

(56) References Cited

U.S. PATENT DOCUMENTS 5,859,205 A * 1/1999 Adair ................ C07K 16/18
7,893,216 B2 * 2/2011 Liu ................ C07K 16/2878
424/130.1

FOREIGN PATENT DOCUMENTS

CN    1673232 A    9/2005

OTHER PUBLICATIONS

MacCallum et al., Antibody-antigen interactions: contact analysis and binding site topography, J. Mol. Biol. 262:732-745, 1996.*
(Continued)

*Primary Examiner* — Claire Kaufman
(74) *Attorney, Agent, or Firm* — Mintz Levin Cohn Ferris Glovsky and Popeo, P.C.

(57) ABSTRACT

The present invention provides a humanized monoclonal antibody against extracellular domain of human death receptor 5, comprising a light chain variable region, whose amino acid sequence has at least 90% identity with the amino acid sequence shown as SEQ ID NO: 1, a heavy chain variable region, whose amino acid sequence has at least 90% identity with the amino acid sequence shown as SEQ ID NO: 2, and constant region derived from human antibody. The present invention also provides nucleotide sequence encoding said humanized monoclonal antibody, a recombinant eukaryotic expression vector, a process for preparing the humanized monoclonal antibody, and the composition and use therefore. Said humanized monoclonal antibody of the present invention shows specific apoptosis-inducing activity against various cancer cells both in vivo and in vitro, and thus it can be used alone or in combination with natural ligand of DR5, apoptosis-inducing ligand associated with tumor nerosis (Continued)

factor or other medicaments for the treatment of a variety of cancers as well as other diseases associated with high DR5 expression.

14 Claims, 4 Drawing Sheets

(51) Int. Cl.
    *C12N 15/10*     (2006.01)
    *A61K 45/06*     (2006.01)
    *A61K 31/704*     (2006.01)
    *C12N 9/64*     (2006.01)
    *A61K 39/00*     (2006.01)

(52) U.S. Cl.
    CPC ............ *A61K 45/06* (2013.01); *C12N 9/6454* (2013.01); *C12Y 304/21075* (2013.01); *A61K 2039/505* (2013.01); *C07K 2317/14* (2013.01); *C07K 2317/24* (2013.01); *C07K 2317/52* (2013.01); *C07K 2317/56* (2013.01); *C07K 2317/565* (2013.01); *C07K 2317/567* (2013.01); *C07K 2317/73* (2013.01); *C07K 2317/92* (2013.01); *C07K 2319/90* (2013.01)

(56) References Cited

OTHER PUBLICATIONS

Lamminmaki et al., Chrystal structure of a recombinant anti-estradiol Fab fragment in complex with the 17beta-estradiol, J. Blol. Chem. 276:36687-94, 2001.*

Rudikoff et al., Single amino acid substitution altering antigen-binding specificity, Proc. Nat. Acad. Sci. USA, 79:1979-1983, Mar. 1982.*

Sela-Culang, et al., The Structural Basis of Antibody-Antigen Recognition. Frontiers in immunology, vol. 4, article 302, pp. 1-13, Oct. 2013.*

Chen et al., Enhancement and destruction of antibody function by somatic mutation: Unequal occurrence is controlled by V gene combinatorial associations, EMBO J., 14 (12): 2784-2794, 1995.*

Jostock et al., Combination of the 2A/furin technology with an animal component free cell line development platform process, Appl. Microbiol. Biotechnol. 87:1517-1524, 2010.*

Ama, Monoclonal antibodies, [Retrieved Online], URL:<http://www.ama-assn.org/ama/pub/physician-resources/medical-science/united-states-adopted-names-council/naming-guidelines/naming-biologics/monoclonal-antibodies.page?#>, Retrieved Oct. 13, 2016, American Medical Association, copyright 1995-2016.*

PRWeb, YORKbiotech Inc. accounces winners of Sanofi Pasteur Healthcare & Biotechnology Venture Challenge 2010, [Retrieved online] URL:<http://www.prweb.com/pdfdownload/4878284.pdf>, Retrieved Oct. 13, 2016, published Dec. 11, 2010.*

Guo, Y. et al. "A Novel Anti-human DR5 Monoclonal Antibody with Tumoricidal Activity Induces Caspase-dependent and Caspase-independent Cell Death". Journal of Biological Chemistry; vol. 280, No. 51. pp. 41940-52. Dec. 23, 2005.

Williams, David G. et al. "Humanising Antibodies by CDR Grafting". Chapter 21 of Antibody Engineering, vol. 1, Eds. Kontermann et al., Springer-Verlag: Berlin, pp. 319-339. 2010.

Hwang, W.Y. et al. "Use of human germline genes in a CDR homology-based approach to antibody humanization". Methods, 36. pp. 35-42. Jan. 17, 2005.

* cited by examiner

HUMANIZED MONOCLONAL ANTIBODIES AGAINST THE EXTRACELLULAR DOMAIN OF HUMAN DEATH RECEPTOR 5

CROSS-REFERENCE TO RELATED APPLICATION

This application claims priority to International Patent Application No. PCT/CN2012/083627, filed Oct. 26, 2012, and entitled "HUMANIZED MONOCLONAL ANTIBODY IN EXTRACELLULAR DOMAIN OF ANTI-HUMAN DEATH RECEPTOR 5". This disclosure is incorporated by reference herein in its entirety.

FIELD OF THE INVENTION

The present invention relates to a humanized monoclonal antibody against the extracellular domain of human death receptor 5, nucleotide sequence encoding the same, a recombinant eukaryotic expression vector which efficiently expresses such humanized monoclonal antibody, a process for preparing said humanized monoclonal antibody, and the use of said humanized monoclonal antibody and the composition thereof.

BACKGROUND

Tumor necrosis factor-related apoptosis-inducing ligand (also named as TRAIL or Apo2L or TNFSF10 for short), which was discovered in 1995, is located on 3q26 of chromosome 3, and a member of tumor necrosis factor (TNF) superfamily. It is a type II transmembrane glycoprotein consisting of 281 amino acids. Its C-terminal is extracellularly located, and has sequence homologous to TNF family. TRAIL receptor 2 (also named as TRAIL-R2 or death receptor 5 or DR5) is widely expressed on the surface of a variety of cancer cells, but not or less expressed on the surface of normal cells. The extracellular region of TRAIL receptor 2 contains the binding region for its natural ligand TRAIL, and the intracellular region contains death domain. Once TRAIL or other agonists bind with DR5, DR5 homotrimerization occurs, and the death domains recruit intracellular relevant signaling proteins to form death-inducing signal complex (DISC), which triggers the downstream cell death signal transduction, thereby specifically induces the death of cancer cells. Previous studies have demonstrated that AD5-10, an agonistic mouse monoclonal antibody against human DR5, is capable of inducing the death of various cancer cells cultivated in vitro, and it also efficiently inhibits in vivo the formation and growth of human xenografted tumor in nude mice, while it is not toxic to normal tissues and cells (Guo Y et al., A novel anti-human DR5 monoclonal antibody with tumoricidal activity induces caspase-dependent and caspase-independent cell death. J Biol Chem 2005; 280 (51):41940-52; WO2006/017961, ZL200410070093.1). This suggests a good prospective clinical application for cancer therapy. However, as a heterogeneous immunoglobulin, murine monoclonal antibody would be recognized by human immune system after it is applied into human body, and then human anti-mouse antibody (HAMA) is generated and attenuates the therapeutic effect as well as possibly damage the human organs. Therefore, an important way to successfully apply murine antibody for therapy of human diseases is to humanize the murine monoclonal antibody, so as to reduce its immunogenicity to human body while maintaining the affinity, specificity and therapeutic efficacy.

The first generation of approach to engineer humanized antibody is to make human-murine chimeric antibody by linking the variable region of murine antibody to the constant region of human antibody. Even though the affinity of original murine antibody is well maintained, due to the spatial separation of the chimeric antibody variable and constant regions, the intact murine antibody variable region still may cause HAMA response. On the basis of chimeric antibodies, complementarity determining region (CDR) grafting technology (Williams D. G. et al., Humanising Antibodies by CDR Grafting in Antibody Engineering (2010) Vol. 1, p319-339, edited by Kontermann R. and Dübel S., Springer-Verlag Berlin Heidelberg) is further used to replace the relatively conserved framework regions (FR) of murine monoclonal antibody variable region with human FR region, and merely maintains the antigen-binding CDR region, so as to construct functional humanized monoclonal antibody. This makes it possible to minimize the immunogenicity of murine antibody molecule. Meanwhile, FR region not only functions as a framework supporting antibody molecules, but also involves in forming the correct conformation when antigen binds to antibody. Therefore, key amino acid residues in humanized antibody molecule FR region shall be subjected to back mutation to maximize the affinity and specificity of murine antibody. Further, since only several amino acid residues in heavy chain and light chain variable region complementarity determining regions (CDRs) and framework regions (FRs) are derived from the immunized animal species, all of the other parts are derived from human same isotype antibody, this minimizes human response against mouse antibody while maintaining specificity and affinity of murine monoclonal antibody, prolongs its half-life in vivo and improves its pharmacokinetic properties. Furthermore, humanized antibody has effector functions of human antibody, such as antibody-dependent cellular cytotoxicity (ADCC) and complement-dependent cellular cytotoxicity (CDCC), thus is more conducive to clinical application.

Mammalian cell expression system possesses intact transcriptional, translational and post-translational processing as well as secretory mechanism, and can efficiently produce an intact antibody molecule with correct folding, assembly, spatial conformation and good biological activity. Such cell expression system is ideal system for humanized antibody production. Thus, the construction of eukaryotic expression vector is very crucial for increasing expression level of humanized antibody. An ideal eukaryotic expression vector needs a strong promoter and a proper selectable marker, which benefit not only the amplification of gene itself, but also the selection of positive cells.

Therefore, the technical purpose of present invention is to produce a novel humanized monoclonal antibody against human DR5 and the eukaryotic expression vector thereof, as well as the use of said humanized monoclonal antibody in the treatment of various cancers.

SUMMARY OF THE INVENTION

The technical purpose of present invention is to provide a humanized monoclonal antibody against human DR5.

Thus, the first aspect of present invention refers to a humanized monoclonal antibody against the extracellular domain of human DR5, comprising a light chain variable region, whose amino acid sequence has at least 90% identity with the amino acid sequence shown as SEQ ID NO: 1, a heavy chain variable region, whose amino acid sequence has at least 90% identity with the amino acid sequence shown as SEQ ID NO: 2, and a constant region of human antibody.

Preferably, the heavy chain constant region of said humanized monoclonal antibody is constant region of human antibody IgG1, and light chain constant region is κ chain of human antibody.

Preferably, the amino acid sequences of light chain variable regions of CDRL1, CDRL2 and CDRL3 of said humanized monoclonal antibody are as follows:
CDRL1: RSSQSLVHSNGNTYLH (SEQ ID NO: 3);
CDRL2: KVSNRFS (SEQ ID NO: 4);
CDRL3: FQSTHVPHT (SEQ ID NO: 5); and/or
the amino acid sequences of heavy chain variable regions of CDRH1, CDRH2 and CDRH3 of said humanized monoclonal antibody are as follows:

CDRH1:
(SEQ ID NO: 6)
DFSMN;

CDRH2:
(SEQ ID NO: 7)
WINTETGEPTYADDFKG;

CDRH3:
(SEQ ID NO: 8)
IDY.

Preferably, the amino acid sequences of framework regions of FRL1, FRL2, FRL3 and FRL4 in light chain variable region of said humanized monoclonal antibody are as follows:
FRL1: DaVMTQSPLSLPVTPGEPASISC, wherein amino acid "a" represents I or V (SEQ ID NO: 9);
FRL2: WYLQKPGQSPQLLIY (SEQ ID NO: 10);
FRL3: GVPDRFSGSGSGTDFTLKISRVEAEDVGVYbC, wherein amino acid "b" represents Y or F (SEQ ID NO: 11);
FRL3: FGQGTKLEIKR (SEQ ID NO: 12); and/or The amino acid sequences of framework regions of FRH1, FRH2, FRH3 and FRH4 in heavy chain variable region of said humanized monoclonal antibody are as follows:
FRH1: cdQLVQSGeELKKPGASVKVSCKASGYTFT, wherein amino acid "c" represents Q or E, amino acid "d" represents V or I, amino acid "e" represents S or P (SEQ ID NO: 13);
FRH2: WVRQAPGQGLfWMG, wherein amino acid "f" represents E or K (SEQ ID NO: 14);
FRH3: RFghSiDTSVSTAYLQISSLKAEDTAVYjCkR, wherein amino acid "g" represents V or A, amino acid "h" represents F or L, amino acid "I" represents L or M, amino acid "j" represents Y or F, amino acid "k" represents A or V (SEQ ID NO: 15);
FRH4: WGQGTTVTVSS (SEQ ID NO: 16).

Preferably, said humanized monoclonal antibody comprises light chain variable region whose amino acid sequence has at least 91%, 92%, 93%, 94%, 95%, 96%, 97%, 98%, 99% and 100% identity with the amino acid sequence shown as SEQ ID NO: 1, and heavy chain variable region whose amino acid sequence has at least 91%, 92%, 93%, 94%, 95%, 96%, 97%, 98%, 99% and 100% identity with the amino acid sequence shown as SEQ ID NO: 2. Preferably, the amino acid sequence of said humanized monoclonal antibody is shown as SEQ ID NO: 17.

Preferably, said humanized monoclonal antibody is selected from the group consisting of AD10, AD14 and AD15, wherein the amino acid sequence for heavy chain and light chain of AD10 is shown as SEQ ID NO: 18 and SEQ ID NO: 19, respectively; the amino acid sequence for heavy chain and light chain of AD14 is shown as SEQ ID NO: 20 and SEQ ID NO: 21, respectively; the amino acid sequence for heavy chain and light chain of AD15 is shown as SEQ ID NO: 22 and SEQ ID NO: 23, respectively.

The second aspect of present invention refers to a nucleotide sequence encoding the humanized monoclonal antibody against the extracellular domain of human DR5 according to the first aspect, preferably, said coding nucleotide sequence comprises sequence encoding self-cleaving Furin/2A peptide between the nucleotide sequence encoding heavy chain and the nucleotide sequence encoding light chain of humanized monoclonal antibody, wherein said heavy chain consists of heavy chain variable region and heavy chain constant region, and said light chain consists of light chain variable region and light chain constant region. Preferably, the amino acid sequence of heavy chain, Furin/2A peptide and light chain of humanized monoclonal antibody encoded by said nucleotide sequence is shown as SEQ ID NO: 17.

The third aspect of present invention refers to a recombinant eukaryotic expression vector, which stably expresses the humanized monoclonal antibody against extracellular domain of human DR5 according to the first aspect above, wherein said nucleotide sequence encoding the humanized monoclonal antibody according to the second aspect above is effectively cloned into the eukaryotic expression vector to be expressed; preferably, said recombinant eukaryotic expression vector carries a strong CAG promoter (a cytomegalovirus immediate early enhancer and a chicken beta-actin promoter) and a selectable marker of dihydrofolate reductase (dhfr); preferably, said eukaryotic expression vector plasmid is pcDNA3.

The fourth aspect of present invention refers to a process for preparing the humanized monoclonal antibody against extracellular domain of human DR5 according to the first aspect, comprising the following steps:
A) transfecting HEK293 cells with said recombinant eukaryotic expression vector according to the third aspect;
B) purifying humanized monoclonal antibody by specific affinity chromatography.

The fifth aspect of present invention refers to a composition consisting of active ingredient such as the humanized monoclonal antibody against extracellular domain of human DR5 according to the first aspect, and recombinant soluble TRAIL or other anti-cancer agents; preferably, said anti-cancer agent is epirubicin.

The sixth aspect of present invention refers to use of the humanized monoclonal antibody against extracellular domain of human DR5 according to the first aspect, the nucleotide sequence of the second aspect which encodes the humanized monoclonal antibody against extracellular domain of human DR5 of the first aspect, the recombinant eukaryotic expression vector of the third aspect which stably expresses the humanized monoclonal antibody against extracellular domain of human DR5 of the first aspect, or the composition according to the fifth aspect which is consisting of the humanized monoclonal antibody against extracellular domain of human DR5 of the first aspect as active ingredient and other anti-cancer agent, in the preparation of a medicament for the treatment of cancers; preferably said cancer is selected from the group consisting of leukemia, liver cancer, colon cancer, lung cancer, ovarian cancer and etc.

In other words, in order to achieve the purpose of present invention, the present invention provides a humanized monoclonal antibody, wherein the amino acid sequences of its light chain and heavy chain variable regions comprise light chain variable region (VL) amino acid sequence which has at least 90%, preferably at least 91%, 92%, 93%, 94%, 95%, 96%, 97%, 98%, 99% and 100% identity with the amino acid sequence shown as SEQ ID NO: 1; and heavy chain variable region (VH) amino acid sequence which has at least 90%, preferably at least 91%, 92%, 93%, 94%, 95%, 96%, 97%, 98%, 99% and 100% identity with the amino acid sequence shown as SEQ ID NO: 2.

The amino acid sequences of light chain variable regions of CDRL1, CDRL2 and CDRL3 of said humanized monoclonal antibody are as follows:
CDRL1 (from amino acid position 24 to 39): RSSQSLVH-SNGNTYLH (SEQ ID NO: 3);
CDRL2 (from amino acid position 55 to 61): KVSNRFS (SEQ ID NO: 4);
CDRL3 (from amino acid position 94 to 102): FQSTHVPHT (SEQ ID NO: 5);
the amino acid sequences of heavy chain variable regions of CDRH1, CDRH2 and CDRH3 of said humanized monoclonal antibody are as follows:

```
CDRH1 (from amino acid position 31 to 35):
                                   (SEQ ID NO: 6)
DFSMN;

CDRH2 (from amino acid position 50 to 66):
                                   (SEQ ID NO: 7)
WINTETGEPTYADDFKG;

CDRH3 (from position amino acid 99 to 101):
                                   (SEQ ID NO: 8)
IDY.
```

The amino acid sequences of framework regions in light chain variable region of FRL1, FRL2, FRL3 and FR4 of said humanized monoclonal antibody are as follows:
FRL1, from amino acid position 1 to 23: DaVMTQS-PLSLPVTPGEPASISC, wherein amino acid "a" represents I or V (SEQ ID NO: 9);
FRL2, from amino acid position 40 to 54: WYLQK-PGQSPQLLIY (SEQ ID NO: 10);
FRL3, from amino acid position 62 to 93: GVPDRFSGSGS-GTDFTLKISRVEA EDVGVYbC, wherein amino acid "b" represents Y or F (SEQ ID NO: 11);
FRL3, from amino acid position 103 to 113: FGQGT-KLEIKR (SEQ ID NO: 12); and/or the amino acid sequences of framework regions in heavy chain variable region of FRH1, FRH2, FRH3 and FRH4 of said humanized monoclonal antibody are as follows:
FRH1, from amino acid position 1 to 30: cdQLVQSGeELK-KPGASVKVSC KASGYTFT, wherein amino acid "c" represents Q or E, amino acid "d" represents V or I, amino acid "e" represents S or P (SEQ ID NO: 13);
FRH2, from amino acid position 36 to 54: WVRQAPGQGLfWMG, wherein amino acid "f" represents E or K (SEQ ID NO: 14);
FRH3, from amino acid position 67 to 98: RFghSiDTS-VSTAYLQISSLKAEDTAV YjCkR, wherein amino acid "g" represents V or A, amino acid "h" represents F or L, amino acid "i" represents L or M, amino acid "j" represents Y or F, amino acid "k" represents A or V (SEQ ID NO: 15);
FRH4, from amino acid position 102 to 112: WGQGTTVT-VSS (SEQ ID NO: 16).

The present invention also provides a process for preparing a humanized monoclonal antibody against extracellular region of DR5, the amino acid sequences of light chain and heavy chain variable region of such humanized monoclonal antibody comprise the amino acid sequence of light chain variable region (VL) shown as SEQ ID NO: 1 and the amino acid sequence of heavy chain variable region (VH) shown as SEQ ID NO: 2, the light chain constant region of said humanized monoclonal antibody is κ chain of human antibody, the subtype of heavy chain constant region is human IgG1. This preparation process comprises the following steps: obtaining the cDNA fragments for heavy chain and light chain variable region of humanized monoclonal antibody separately by PCR and splicing PCR using synthetic primers; constructing the obtained cDNA fragments for variable regions into pCP vector by homologous recombination; linking to human IgG1 heavy chain constant region and κ chain, respectively; and then linking the heavy chain of humanized monoclonal antibody to the light chain of humanized monoclonal antibody by overlap PCR; inserting a sequence which encodes the self-cleaving Furin/2A peptide between the heavy chain and light chain.

The gene of the above mentioned humanized monoclonal antibody is cloned into pcDNA3 vector, which is used as starting vector, to construct a new eukaryotic expression vector comprising CAG promoter and dhfr selectable marker, to express the humanized anti-human DR5 monoclonal antibody. The new expression vector provided in present invention contains the sequence, which encodes the self-cleaving Furin/2A peptide, and heavy chain and light chain of humanized monoclonal antibody are linked into a single open reading frame. In particular, said eukaryotic expression vector contains strong CAG promoter, dhfr selectable marker, coding sequence of heavy chain variable region consisting of heavy chain complementarity determining region derived from mouse anti-human DR5 monoclonal antibody (AD5-10) and heavy chain framework region derived from human antibody, coding sequence of light chain variable region consisting of light chain complementarity determining region derived from mouse anti-human DR5 monoclonal antibody (AD5-10) and light chain framework region derived from human antibody, coding sequences of human IgG1 heavy chain constant region and light chain constant κ chain, and coding sequence of self-cleaving Furin/2A peptide inserted between heavy chain and light chain; the above fragments are effectively linked together to efficiently express said humanized monoclonal antibody. Preferably, said mouse anti-human DR5 monoclonal antibody is AD5-10 (Guo Y et al., A novel anti-human DR5 monoclonal antibody with tumoricidal activity induces caspase-dependent and caspase-independent cell death. J Biol Chem 2005; 280 (51):41940-52; WO2006/017961, ZL200410070093.1).

Preferably, the following is linked to form a nucleotide sequence which encodes amino acid sequence (HF2AL): the coding sequences of heavy chain variable region and light chain variable region (the heavy chain variable region consists of heavy chain complementarity determining region derived from mouse anti-human DR5 monoclonal antibody AD5-10 and heavy chain framework region derived from human antibody, and the light chain variable region consists of light chain complementarity determining region derived from mouse anti-human DR5 monoclonal antibody AD5-10 and light chain framework region derived from human antibody, respectively), coding sequences of human IgG1 heavy chain constant region and light chain constant κ chain, and coding sequence of self-cleaving Furin/2A peptide (F2A) inserted between heavy chain (H) and light chain (L); wherein the amino acid sequence (HF2AL) is shown as:

(SEQ ID NO: 17)
GSMEFGLSWLFLVAILKGVQCcdQLVQSGeELKKPGASVKVSCKASG

YTFTDFSMNWVRQAPGAGLfWMGWINTETGEPTYADDFKGRFghSiD

TSVSTAYLQISSLKAEDTAVYjCkRIDYWGQGTTVTVSSASTKGPSV

FPLAPSSKSTSGGTAALGCLVKDYFPEPVTVSWNSGALTSGVHTFPA

VLQSSGLYSLSSVVTVPSSSLGTQTYICNVNHKPSNTKVDKKVEPKS

CDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDW

LNGKEYKCKVSNKALPAPIEKTISKAKGQPREPQVYTLPPSRDELTK

NQVSLTCLVKGFYPSDIAVEWESNGQPENNYKTTPPVLDSDGSFFLY

SKLTVDKSRWQQGNVFSCSVMHEALHNHYTQKSLSLSPGKRKRRA*PV*

*KQTLNFDLLKLAGDVESNPG*PDMRVPAQLLGLLLLWFPGSRCDaVMT

QSPLSLPVTPGEPASISCRSSQSLVHSNGNTYLHWYLQKPGQSPQLL

IYKVSNRFSGVPDRFSGSGSGTDFTLKISRVEAEDVGVYbCFQSTHV

PHTFGQGTKLEIKRTVAAPSVFIFPPSDEQLKSGTASVVCLLNNFYP

REAKVQWKVDNALQSGNSQESVTEQDSKDSTYSLSSTLTLSKADYEK

HKVYACEVTHQGLSSPVTKSFNRGECZLE, wherein, the amino acid sequence in italic represents F2A, the sequence before F2A represents the heavy chain of humanized monoclonal antibody, the sequence following F2A represents the light chain of humanized monoclonal antibody; amino acid "a" represents I or V, amino acid "b" represents Y or F, amino acid "c" represents Q or E, amino acid "d" represents V or I, amino acid "e" represents S or P, amino acid "f" represents E or K, amino acid "g" represents V or A, amino acid represents F or L, amino acid "i" represents L or M, amino acid "j" represents Y or F, amino acid "k" represents A or V. As for the above amino acids from "a" to "k", the alternatives represent corresponding human antibody amino acids or murine antibody amino acids via back mutation, respectively. Those alternatives per se are constitutional amino acids of antibody framework region, therefore, it is possible that there are certain differences in activity and/or antigenicity among the antibodies comprising these alternatives, however, the antibodies comprising these alternatives are still within the scope of humanized monoclonal antibody against human DR5 according to the present invention, there is not substantial difference among these antibodies.

HEK293 cells are transfected with eukaryotic expression vector of humanized monoclonal antibody against DR5, the intact humanized monoclonal antibody against DR5 with strong killing activity to various cancer cells and purified by affinity chromatography is named as zaptuzumab.

Both this humanized monoclonal antibody and TRAIL (the natural ligand for DR5) are capable of binding to DR5, whereas the binding sites are different.

In vitro studies show that this humanized anti-DR5 monoclonal antibody is able to kill a variety of cancer cells, such as leukemia, liver cancer, colon cancer, lung cancer and etc., the killing activity is time- and dose-dependent. Since the humanized monoclonal antibody plays its role via binding with DR5, on the basis of the fact that the examples of present invention have demonstrated that said antibody can kill the mentioned cancer cells, it is reasonable to believe that other types of malignant cancer cells with DR5 expression would also be killed and thereby the purpose of treating corresponding malignant cancers is achieved.

The humanized anti-DR5 monoclonal antibody induces two different forms of cell death, apoptosis and autophagic death.

In vivo studies show that humanized anti-DR5 monoclonal antibody strongly inhibits growth of xenograft cancer cells, such as human colon cancer, liver cancer and lung cancer, in nude mice, and can be used in combination with recombinant TRAIL or anti-cancer agent such as epirubicin to achieve better therapeutic efficacy. No significant rebound phenomenon is observed after the medicament is discontinued. No pathological changes are observed in organs (including mouse liver and kidney) by histological analysis.

The combination of humanized anti-DR5 monoclonal antibody produced in the present invention and recombinant TRAIL or anti-cancer agents such as epirubicin has synergistic activity in killing of various cancer cells.

The present invention also provides use of said humanized monoclonal antibody of the present invention in the preparation of medicament for the treatment of cancers.

Finally, the present invention also provides use of a recombinant expression vector in the preparation of antibody medicament for antibody gene therapy of cancers, wherein said recombinant expression vector is constructed by inserting the humanized monoclonal antibody or an antibody having at least 80%, preferably at least 85%, 90%, 91%, 92%, 93%, 94%, 95%, 96%, 97%, 98% or 99% homology with said humanized monoclonal antibody into the pharmaceutically acceptable carrier.

As seen, in the present invention, anti-DR5 humanized monoclonal antibody and the eukaryotic expression vector are prepared by using modern biological techniques and methods such as genetic engineering; and then HEK293 cells are transfected with this expression vector and large numbers of the novel humanized anti-DR5 monoclonal antibody expressed. In vitro, such humanized monoclonal antibody has ability of strongly inducing apoptosis of various cancer cells; in vivo, such humanized monoclonal antibody has biological activity of significantly inhibiting the tumorigenesis of human xenograft tumor cells and the growth of human xenograft tumor in nude mice; when combined with other anti-cancer agents, the humanized monoclonal antibody induces both in vitro and in vivo death of cancer cells, enhances the efficacy of chemotherapeutic agent and reduces the dose and side effects of chemotherapeutic agent. Thus, such humanized monoclonal antibody is important for the development and application of novel anti-cancer agents.

The advantages and effects of the present invention are to obtain a humanized anti-DR5 monoclonal antibody and its eukaryotic expression vector, which have not been reported before. In said eukaryotic expression vector, the heavy chain and light chain of said humanized monoclonal antibody are linked within an open reading frame, thus, it can expresses heavy chain and light chain of the humanized monoclonal antibody in a simultaneous, balanced and matching way, and then they are automatically assembled into one humanized monoclonal antibody molecule with complete functions.

The binding site, at which said humanized monoclonal antibody binds with DR5, is different from that TRAIL binds with DR5; therefore said humanized monoclonal antibody can be combined with TRAIL and anti-cancer agents like epirubicin in order to synergistically enhance its anti-cancer efficacy. Said humanized monoclonal antibody is able to induce in vitro apoptosis of various cancer cells, while shows no toxic side effects on normal cells. Said humanized monoclonal antibody has in vivo anti-cancer activity of strongly inhibiting the formation and growth of human xenograft tumor, while has no toxic side effects on the organs like liver and kidney in normal mice. These show that this humanized monoclonal antibody can be developed into safe and effective anti-cancer agents. The recombinant expression vector obtained by inserting the nucleotide sequence, which encodes said humanized monoclonal antibody or further modified humanized antibody into pharmaceutically acceptable carrier, can also be used to prepare antibody medicament for the antibody gene therapy of cancers.

Humanized anti-DR5 monoclonal antibody is an intact humanized monoclonal antibody, which is constructed by linking murine anti-DR5 antibody variable region to human antibody constant region using genetic engineering techniques, and it reduces human response against mouse antibody while maintaining specificity and affinity of the original monoclonal antibody, prolongs its half-life and improves its pharmacokinetic properties, and also effectively activates immune responses associated with complement and Fc receptor.

Based on a functional murine anti-human DR5 monoclonal antibody (AD5-10), which has been prepared, the present invention establishes a humanized monoclonal antibody by CDR grafting strategy. Said antibody shows specific apoptosis-inducing activity against many cancer cells both in vivo and in vitro, while shows no toxic side effects on normal cells and tissues; and thus it can be used alone or combined with TRAIL or other anti-cancer agents for the treatment of various cancers as well as other diseases related to the high level expression of DR5.

DETAILED DESCRIPTION OF THE INVENTION

Figure 1:
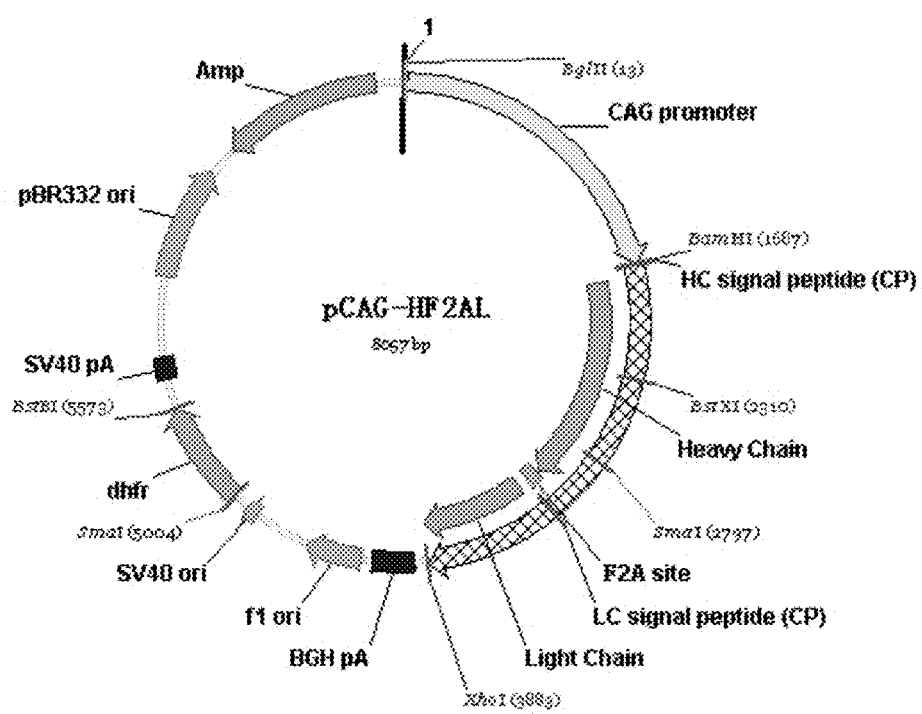
FIG. 1 shows the structural diagram showing the eukaryotic expression vector of humanized anti-DR5 monoclonal antibody, which contains CAG promoter and dhfr selectable marker. ADHFL (1692) represents the nucleotide sequence, which encodes heavy chain of humanized anti-DR5 monoclonal antibody, Furin/2A peptide and light chain of humanized anti-DR5 monoclonal antibody.

The present invention is further illustrated by the following non-limiting examples, it will be appreciated by those skilled in the art that various modifications to the present invention can be carried out without deviating from the spirit of present invention, and thus also fall into the scope of present invention.

Unless clearly indicated, the experiment processes below are routine methods; unless clearly indicated, the experiment materials used are easily commercially available.

EXAMPLES

Example 1

Design of Humanized Monoclonal Antibody, and Construction and Results of Eukaryotic Expression Vector, which Efficiently Expresses Humanized Anti-DR5 Monoclonal Antibody The CDR fragments of heavy chain and light chain variable regions of murine AD5-10 monoclonal antibody (Chinese patent application No. 200410070093.1) were identified and labeled using Kabat numbering system (such as, for example, as described online at www.bioinf.org.uk). The canonical structural prediction for CDR fragments of heavy chain and light chain variable regions was performed according to reference documents (1, Williams D. G. et al. Humanising Antibodies by CDR Grafting in Antibody Engineering (2010) Vol. 1, p319-339, Editors: Kontermann R. and Dubel S., Springer-Verlag Berlin Heidelberg. 2, Hwang WY, Almagro JC et al., (2005) Methods, 36: 35-42), human antibody sequences which share the same canonical structure were chosen as recipient framework.

Design of humanized antibody heavy chain: the amino acids supporting CDR structure and VH/VL interface were identified and back-mutated into murine antibody sequences. The sequences subjected to back mutation were aligned with all human antibody sequences which share the same canonical structure, and then the most similar human antibody sequence was selected and used to perform CDR grafting. Then, it was aligned with all of the same kind antibody sequences within IMGT database; in order to reduce immunogenicity, specific amino acids would be mutated into common amino acids as far as possible. If the first amino acid at N terminus is Q, it would be modified into E. Meanwhile, key amino acids selected by using construction model were subjected to back mutation. The humanized antibody sequence was confirmed not to be incorporated with glycosylation sites. The selection of humanized antibody J-region was entirely based on sequence similarity.

Design of humanized antibody light chain was performed by using the same method as above.

Antibody homology modeling: AD10-5 light chain and heavy chain as well as BLAST SEARCH were respectively used for search in PDB protein structure database to find out human antibodies with known structure which share the highest sequence similarity.

According to the output results and sequence similarity reported by BLAST SEARCH, 1DLF, 1I9J, 1NQB and 1PLG were selected as VL modeling templates. 1IAL, 1NLB, 1A4K and 1FJ1 were selected as VH template; homology modeling for VH and VL was performed by using Schrodinger software package, and structural models of light chain and heavy chain were obtained. And then, contact program in CCP4 software package was used to analyze the structural models, and the amino acid residues in light and heavy chain framework region, which interact with CDR loop were listed. According to the results of software analysis and artificial inspection, the following amino acid residues in framework region were found to be more important for maintenance of spatial conformation of CDR loop: they were light chain amino acid residues D60, D70, Y49, F71, M4 and V2; heavy chain amino acid residues K46, W47, M48, F67, L69, M71, W102 and 12. The amino acid sequence of such designed heavy chain of humanized antibody, Furin/2A peptide and light chain of humanized antibody is shown as SEQ ID NO: 17. After optimization, the amino acid sequences of heavy chain and light chain for three humanized antibodies AD10, AD14 and AD15 are shown as SEQ ID NO: 18 and 19, SEQ ID NO: 20 and 21, and SEQ ID NO: 22 and 23, respectively.

PcDNA3 (Invitrogen, A-150228) was used as a starting vector, pAM/CAG vector (provided by University of Hong Kong) was used as template, forward primer 5'GGCGCA-GATCTATTGACGTCAAT3' (SEQ ID NO: 24) and reverse primer 5'GGCAAGCTTAATTCTTTGCCAAAATG3' (SEQ ID NO: 25) were used to amplify CAG promoter sequence (a modified cytomegalovirus immediate early enhancer and a chicken beta-actin promoter). With pSV2-dhfr vector DNA (purchased from ATCC, 67110) used as a template, forward primer 5'AATCCCGGGACAGCTCAGGGCTGC G3' (SEQ ID NO: 26) and reverse primer 5'GGCGGCGCT-TCGAAAAAGCCAGCAA AAGCTC3' (SEQ ID NO: 27) were used to amplify dihydrofolate reductase (dhfr) gene fragment. The cDNA fragments of humanized monoclonal antibody heavy chain and light chain variable regions were obtained by amplifying with splicing PCR or chemical synthesis, and such obtained variable region cDNA fragments were integrated into linearized pCP vector (provided by Shanghai Wisdom Chemical Ltd Co.) with universal sequence of human IgG1 heavy chain constant region by using homologous recombination technique. The coding sequence for self-cleaving site Furin/2A peptide (F2A) was amplified by PCR (primer 1: 5' CAGAAGAGCCTCTC-CCTGTCTCCGGG TAAAAGGAAGAGGCGAGCAC-CTGT 3' (SEQ ID NO: 28), primer 2: 5' GCCCAGC AGCTGGGCGGGCACGCGCATGTCGGGCCCAGGAT-TGGACTCA 3' (SEQ ID NO: 29), and inserted between nucleotide sequences encoding the humanized monoclonal antibody heavy chain and light chain in recombinant plasmid obtained above, therefore an open reading frame (OPF) was formed in the following order: nucleotide sequence encoding CAG, the humanized antibody heavy chain (H), Furin/2A peptide (F2A), the humanized antibody light chain (L) (denoted as HF2AL), and nucleotide sequence encoding dhfr.

The nucleotide sequence encoding OPF obtained above was inserted into the original vector pcDNA3, and confirmed correctly by sequencing analysis. The novel eukaryotic expression vector expressing humanized anti-DR5 monoclonal antibody was obtained (named as pcDNA3-CAG-HF2AL-dhfr). The map for thus obtained recombinant expression plasmid is shown in FIG. 1.

Example 2

Expression and Purification of Humanized Anti-DR5 Monoclonal Antibody

Figure 2:
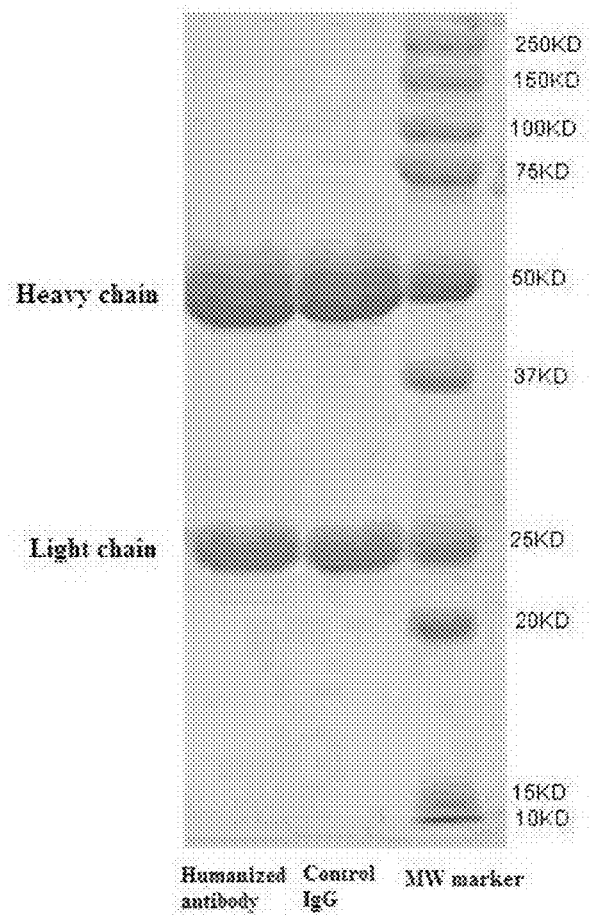
FIG. 2 shows the results of humanized anti-DR5 monoclonal antibody by SDS-PAGE assay, wherein the humanized anti-DR5 monoclonal antibody was obtained by transfecting HEK293 cells with the eukaryotic expression vector of said humanized monoclonal antibody, then purifying from the cell culture supernatant by using affinity chromatography.

The constructed eukaryotic expression vector pcDNA3-CAG-HF2AL-dhfr was transfected into HEK293 cells (purchased from ATCC, CRL-9096) by liposome transfection. The cells were incubated at 37° C., 5% $CO_2$, with shaking at 120 rpm/min; the humanized anti-DR5 monoclonal antibody was expressed by HEK293 eukaryotic cells and secreted into cell culture medium. Cell culture supernatant was collected when the viability of transfected cells reached less than 60% (about 6 days). One ml of protein A affinity chromatography column was prepared, firstly balanced with PBS phosphate buffer (20 mM phosphate, 300 mM sodium chloride, pH7.0), and then loaded with collected cell culture supernatant, washed with PBS phosphate buffer, and eluted with 100 mM citric acid (pH 3.0). The collected eluent was immediately adjusted with 1.0 M Tris-HCl (pH 9.0) to pH 8.0, and then dialyzed against PBS buffer overnight. The purity and molecular weight of humanized anti-DR5 monoclonal antibody was subjected to SDS-PAGE analysis. The results are shown in FIG. 2.

Example 3

Affinity Assay of Humanized Anti-DR5 Monoclonal Antibody Binding to its Antigen DR5

Figure 3:
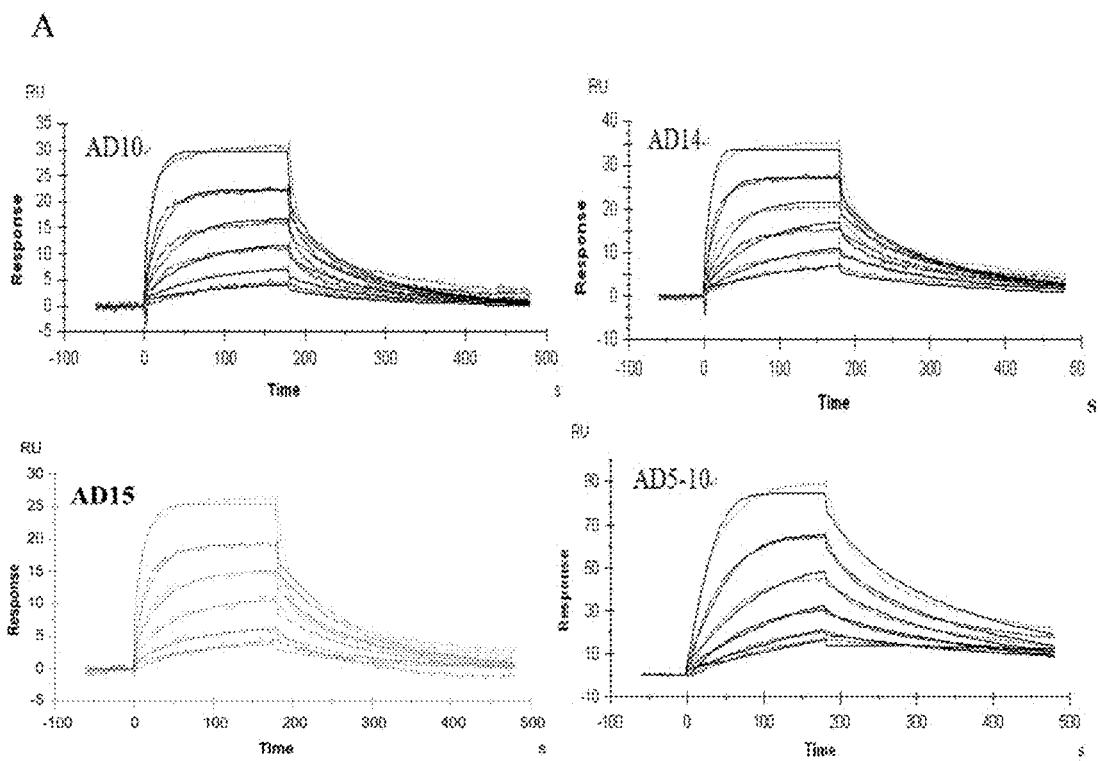
FIG. 3 shows the affinities of three strains of humanized monoclonal antibodies (AD10, AD14 and AD15) to the antigen DR5, measured by using Biacore system and CM5 chip. The four panels in figure A (from left to right, from top to bottom) correspond to the affinity profiles of AD10, AD14, AD15 and AD5-10 to the antigen DR5, respectively. Figure B shows the corresponding affinity calculated according to figure A.

On CM5 chip (GE Healthcare, BR-1000-14) used by Biacore X100 system (GE Healthcare, Uppsala, Sweden), blank control channel and sample channels were selected. Firstly, a mixture of 50 mM N-hydroxysuccinimide (NHS) and 200 mM carbodiimide [1-ethyl-3-3-dimethyl aminopropyl carbodiimide, EDC] at a ratio of 1:1 was injected into blank control channel and sample channels at a speed of 10 µl/min for 7 minutes to activate the chip. The antigen DR5 (45 µg/ml) dissolved in sodium acetate solution, pH 5.5, was injected at a speed of 5 µl/min to coat the chip, until signal with target value 680 Ru was achieved. 1.0 M ethanolamine was injected at a speed of 10 µl/min for 7 minutes, to block the excess binding sites on the chip. The binding kinetics assay was performed by using HBS-EP buffer (0.01 M HEPES, pH 7.4, 0.15 M NaCl, 3 mM EDTA, 0.005% Surfactant P20), the purified humanized monoclonal antibodies AD10, AD14 and AD15 were diluted into various concentrations, and injected into blank control channel and sample channels at a speed of 30 µl/min for 3 minutes respectively. HBS-EP buffer was injected at a speed of 30 µl/min for 5 minutes to perform dissociation. Data analysis and process were performed by using Biacore X100 evaluation 2.0 software. The results are shown in FIG. A and B of FIG. 3.

The results show that the humanized monoclonal antibodies maintain the antigen affinity of their parental murine anti-human DR5 monoclonal antibody (AD5-10).

Example 4

Figure 4:
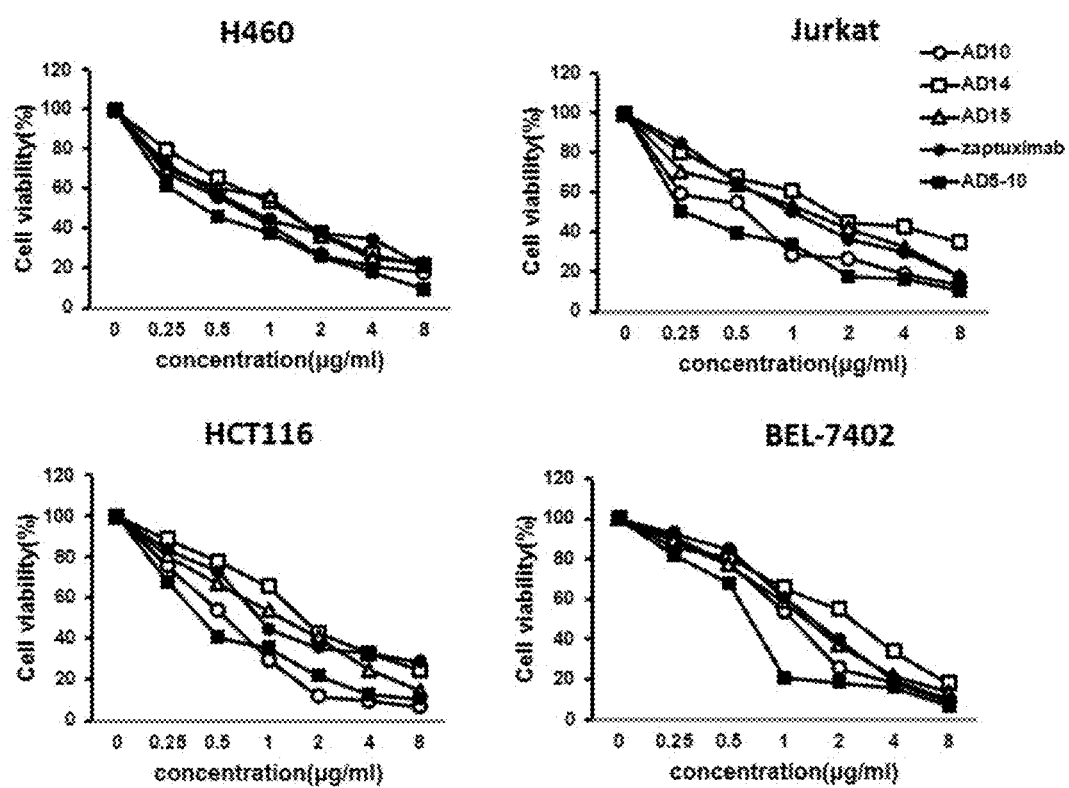
FIG. 4 shows the in vitro activity of humanized monoclonal antibody in killing cancer cells. The human T cell lymphoblastic leukemia Jurkat, liver cancer cells BEL-7402, lung cancer cells H460 and colon cancer cells HCT116 were treated for 24 hours with said humanized monoclonal antibody AD10, AD14 and AD15 at different concentrations. The survival rates of cancer cells were measured by using CCK-8 cytotoxicity assay kit.

Activity Assay of Humanized Anti-Human DR5 Monoclonal Antibody in Killing Cancer Cells The assay was carried out in 96-well cell culture plates. Various concentrations (0, 0.5, 1, 2, 4, 8 µg/ml) of humanized anti-human DR5 monoclonal antibodies AD10, AD14 and AD15 were separately added into to human T-cell lymphocytic leukemia cells Jurkat (ATCC, TIB-152), colon cancer cells HCT116 (ATCC, CCL-247), liver cancer cells BEL-7402 (cell bank, Shanghai Institutes for Biological Sciences of Chinese Academy of Sciences, TCHu 10) and non-small cell lung cancer cells H460 (ATCC, HTB-177) in logarithmic growth phase, for 24 hours; parental murine anti-human DR5 monoclonal antibody (AD5-10) and human-mouse chimeric antibody zaptuximab were used as controls. According to the protocol of CCK-8 cytotoxicity detection kit (Dojindo, Gaithersburg, Md.), CCK-8 agents were added and incubated for 2 to 4 hours, the OD value was measured at 450 nm wavelength in micro-ELISA plate detector. The OD value in cell-free well was set as blank control "0". Cell survival rate=OD value in treated well/OD value in untreated well. The results are shown in FIG. 4.

The results show that the above humanized monoclonal antibodies have significant activity in killing various cancer cells.

Those skilled in the art understand that the particular sequence of said humanized monoclonal antibody disclosed in present invention is allowed to be properly modified, provided that the affinity and biological activity of said humanized monoclonal antibody of present invention are not changed. For example, partial amino acid residues in said sequence may be deleted, added and substituted without modifying the affinity and biological activity of said sequence. For example, partial amino acid residues in said CDR and FR regions of present invention may be replaced by amino acids with similar nature without affecting its affinity and biological activity. The coding sequences of said humanized monoclonal antibody can be substituted accordingly based on different codon preference of their hosts.

What is claimed is:

1. A humanized monoclonal antibody against extracellular domain of human death receptor 5, comprising:
   a light chain variable region, whose amino acid sequence is shown as SEQ ID NO: 1,
   a heavy chain variable region, whose amino acid sequence is shown as SEQ ID NO: 2, and
   a constant region derived from a human antibody.

2. The humanized monoclonal antibody against extracellular domain of human death receptor 5 according to claim 1, wherein the heavy chain constant region of said humanized monoclonal antibody is a constant region of a human antibody IgG1, and the light chain constant region is a κ chain of human antibody.

3. The humanized monoclonal antibody against extracellular domain of human death receptor 5 according to any of claim 1 or 2, wherein:
   the light chain variable region comprises amino acid sequences CDRL1, CDRL2 and CDRL3 of said humanized monoclonal antibody as follows,
   CDRL1: RSSQSLVHSNGNTYLH (SEQ ID NO: 3);
   CDRL2: KVSNRFS (SEQ ID NO: 4);
   CDRL3: FQSTHVPHT (SEQ ID NO: 5); and
   The heavy chain variable region comprises amino acid sequences CDRH1, CDRH2 and CDRH3 of said humanized monoclonal antibody as follows,
   CDRH1: DFSMN (SEQ ID NO: 6);
   CDRH2: WINTETGEPTYADDFKG (SEQ ID NO: 7);
   CDRH3: IDY (SEQ ID NO: 8).

4. The humanized monoclonal antibody against the extracellular domain of human death receptor 5 according to any of claims 1 or 2, wherein:
   the amino acid sequences of framework regions FRL1, FRL2, FRL3 and FRL4 in the light chain variable region of said humanized monoclonal antibody are as follows,
   FRL1: DaVMTQSPLSLPVTPGEPASISC, wherein amino acid "a" represents I or V (SEQ ID NO: 9);
   FRL2: WYLQKPGQSPQLLIY (SEQ ID NO: 10);
   FRL3: GVPDRFSGSGSGTDFTLKISRVEAED-VGVYbC, wherein amino acid "b" represents Y or F (SEQ ID NO: 11);
   FRL4: FGQGTKLEIKR (SEQ ID NO: 12); and/or
   the amino acid sequences of framework regions FRH1, FRH2, FRH3 and FRH4 in the heavy chain variable region of said humanized monoclonal antibody are as follows,
   FRH1: cdQLVQSGeELKKPGASVKVSCKASGYTFT, wherein amino acid "c" represents Q or E, amino acid "d" represents V or I, amino acid "e" represents S or P (SEQ ID NO: 13);
   FRH2: WVRQAPGQGLfWMG, wherein amino acid "f" represents E or K (SEQ ID NO:14);
   FRH3: RFghSiDTSVSTAYLQISSLKAEDTAVYjCkR, wherein amino acid "g" represents V or A, amino acid "h" represents F or L, amino acid "i" represents L or M, amino acid "j" represents Y or F, and amino acid "k" represents A or V (SEQ ID NO: 15); and
   FRH4: WGQGTTVTVSS (SEQ ID NO: 16).

5. The humanized monoclonal antibody against the extracellular domain of human death receptor 5 according to any of claims 1 or 2, wherein the amino acid sequence of said humanized monoclonal antibody is shown as SEQ ID NO: 17.

6. The humanized monoclonal antibody against extracellular domain of human death receptor 5 according to any one of claims 1 or 2, wherein said humanized monoclonal antibody is selected from the group consisting of AD10, AD14 and AD15, wherein the amino acid sequences for heavy chain and light chain of AD10 are shown as SEQ ID NO: 18 and SEQ ID NO: 19, respectively, the amino acid sequences for heavy chain and light chain of AD14 are shown as SEQ ID NO: 20 and SEQ ID NO: 21, respectively, and the amino acid sequences for heavy chain and light chain of AD15 are shown as SEQ ID NO: 22 and SEQ ID NO: 23, respectively.

7. A nucleotide sequence encoding the humanized monoclonal antibody against extracellular region of human death receptor 5 of any one of claims 1 or 2, said encoding nucleotide sequence comprises a nucleotide sequence encoding self-cleaving Furin/2A peptide between the nucleotide sequence encoding the heavy chain and the nucleotide sequence encoding the light chain of said humanized monoclonal antibody, wherein said heavy chain consists of the heavy chain variable region and the heavy chain constant region, and said light chain consists of the light chain variable region and the light chain constant region.

8. A recombinant eukaryotic expression vector comprising the nucleotide sequence encoding the humanized monoclonal antibody against extracellular region of human death receptor 5 of claim 7, wherein said nucleotide sequence is effectively expressed by said recombinant eukaryotic expression vector; and said recombinant eukaryotic expression vector comprises a strong CAG promoter and a dihydrofolate reductase selectable marker.

9. A process for preparing the humanized monoclonal antibody against extracellular region of human death receptor 5 of any one of claims 1 or 2, comprising the following steps:
   A) transfecting HEK293 cells with said recombinant eukaryotic expression vector of claim 8;
   B) expressing said humanized monoclonal antibody; and
   C) purifying the expressed humanized monoclonal antibody by specific affinity chromatography.

10. A composition consisting of the humanized monoclonal antibody against extracellular domain of human death receptor 5 of any one of claims 1 or 2 as an active ingredient, and TRAIL or another anti-cancer agent.

11. A method for treating cancer, comprising a step of administering a therapeutically effective amount of the humanized monoclonal antibody against extracellular domain of human death receptor 5 of any of claims 1 or 2 and one or more chemotherapeutic agents to a subject, wherein the cancer is selected from leukemia, liver cancer, colon cancer, lung cancer, and ovarian cancer.

12. The nucleotide sequence encoding the humanized monoclonal antibody against extracellular region of human death receptor 5 according to claim 7, wherein the amino acid sequence of said heavy chain, Furin/2A peptide and light chain of the humanized monoclonal antibody encoded by said encoding nucleotide sequence, is shown as SEQ ID NO: 17.

13. The recombinant eukaryotic expression vector according to claim 8, wherein said eukaryotic expression vector is plasmid pcDNA3.

14. The composition according to claim 10, wherein said another anti-cancer agent is epirubicin.

* * * * *

UNITED STATES PATENT AND TRADEMARK OFFICE
CERTIFICATE OF CORRECTION

PATENT NO. : 9,725,517 B2
APPLICATION NO. : 14/435684
DATED : August 8, 2017
INVENTOR(S) : Dexian Zheng et al.

Page 1 of 1

It is certified that error appears in the above-identified patent and that said Letters Patent is hereby corrected as shown below:

On the Title Page

Column 1, Line 12:
In (73) Assignee: please delete "Institute of Basic Medical Sciences, Chinese Academy of Medical Sciences, Beijing (CN)" and insert --OBIO TECHNOLOGY (SHANGHAI) CORP., LTD. (CN)--

Signed and Sealed this
Fourth Day of December, 2018

Andrei Iancu
*Director of the United States Patent and Trademark Office*

SEQUENCE LISTING

<160> NUMBER OF SEQ ID NOS: 29

<210> SEQ ID NO 1
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 1

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ser
                85                  90                  95

Thr His Val Pro His Thr Phe Gly Gln Gly Thr Lys Leu Glu Ile Lys
            100                 105                 110

Arg

<210> SEQ ID NO 2
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 2

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Phe
            20                  25                  30

Ser Met Asn Trp Val Arg Gln Ala Pro Gly Gln Gly Leu Glu Trp Met
        35                  40                  45

Gly Trp Ile Asn Thr Glu Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Ile Asp Tyr Trp Gly Gln Gly Thr Thr Val Thr Val Ser Ser
            100                 105                 110

<210> SEQ ID NO 3
<211> LENGTH: 16
<212> TYPE: PRT
<213> ORGANISM: Artificial sequence
<220> FEATURE:
<223> OTHER INFORMATION: Synthetic polypeptide

<400> SEQUENCE: 3

Arg Ser Ser Gln Ser Leu Val His Ser Asn Gly Asn Thr Tyr Leu His
1               5                   10                  15

<210> SEQ ID NO 4
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 4

Lys Val Ser Asn Arg Phe Ser
1               5

<210> SEQ ID NO 5
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 5

Phe Gln Ser Thr His Val Pro His Thr
1               5

<210> SEQ ID NO 6
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 6

Asp Phe Ser Met Asn
1               5

<210> SEQ ID NO 7
<211> LENGTH: 17
<212> TYPE: PRT
<213> ORGANISM: Artificial sequence
<220> FEATURE:
<223> OTHER INFORMATION: Synthetic polypeptide

<400> SEQUENCE: 7

Trp Ile Asn Thr Glu Thr Gly Glu Pro Thr Tyr Ala Asp Asp Phe Lys
1               5                   10                  15

Gly

<210> SEQ ID NO 8
<211> LENGTH: 3
<212> TYPE: PRT
<213> ORGANISM: Artificial sequence
<220> FEATURE:
<223> OTHER INFORMATION: Synthetic polypeptide

```
<400> SEQUENCE: 8

Ile Asp Tyr
1

<210> SEQ ID NO 9
<211> LENGTH: 23
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Xaa is Ile or Val

<400> SEQUENCE: 9

Asp Xaa Val Met Thr Gln Ser Pro Leu Ser Leu Pro Val Thr Pro Gly
1               5                   10                  15

Glu Pro Ala Ser Ile Ser Cys
            20

<210> SEQ ID NO 10
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 10

Trp Tyr Leu Gln Lys Pro Gly Gln Ser Pro Gln Leu Leu Ile Tyr
1               5                   10                  15

<210> SEQ ID NO 11
<211> LENGTH: 32
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (31)..(31)
<223> OTHER INFORMATION: Xaa is Tyr or Phe

<400> SEQUENCE: 11

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Xaa Cys
            20                  25                  30

<210> SEQ ID NO 12
<211> LENGTH: 11
<212> TYPE: PRT
<213> ORGANISM: Artificial sequence
<220> FEATURE:
<223> OTHER INFORMATION: Synthetic polypeptide

<400> SEQUENCE: 12

Phe Gly Gln Gly Thr Lys Leu Glu Ile Lys Arg
1               5                   10

<210> SEQ ID NO 13
<211> LENGTH: 30
<212> TYPE: PRT
<213> ORGANISM: Artificial sequence
<220> FEATURE:
<223> OTHER INFORMATION: Synthetic polypeptide
<220> FEATURE:
```

<221> NAME/KEY: MISC_FEATURE
<222> LOCATION: (1)..(1)
<223> OTHER INFORMATION: Xaa is Gln or Glu
<220> FEATURE:
<221> NAME/KEY: MISC_FEATURE
<222> LOCATION: (2)..(2)
<223> OTHER INFORMATION: Xaa is Val or Ile
<220> FEATURE:
<221> NAME/KEY: MISC_FEATURE
<222> LOCATION: (9)..(9)
<223> OTHER INFORMATION: Xaa is Ser or Pro

<400> SEQUENCE: 13

Xaa Xaa Gln Leu Val Gln Ser Gly Xaa Glu Leu Lys Lys Pro Gly Ala
1               5                   10                  15

Ser Val Lys Val Ser Cys Lys Ala Ser Gly Tyr Thr Phe Thr
            20                  25                  30

<210> SEQ ID NO 14
<211> LENGTH: 14
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (11)..(11)
<223> OTHER INFORMATION: Xaa is Glu or Lys

<400> SEQUENCE: 14

Trp Val Arg Gln Ala Pro Gly Gln Gly Leu Xaa Trp Met Gly
1               5                   10

<210> SEQ ID NO 15
<211> LENGTH: 32
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (3)..(3)
<223> OTHER INFORMATION: Xaa is Val or Ala
<220> FEATURE:
<221> NAME/KEY: MISC_FEATURE
<222> LOCATION: (4)..(4)
<223> OTHER INFORMATION: Xaa is Phe or Leu
<220> FEATURE:
<221> NAME/KEY: MISC_FEATURE
<222> LOCATION: (6)..(6)
<223> OTHER INFORMATION: Xaa is Leu or Met
<220> FEATURE:
<221> NAME/KEY: MISC_FEATURE
<222> LOCATION: (29)..(29)
<223> OTHER INFORMATION: Xaa is Tyr or Phe
<220> FEATURE:
<221> NAME/KEY: MISC_FEATURE
<222> LOCATION: (31)..(31)
<223> OTHER INFORMATION: Xaa is Ala or Val

<400> SEQUENCE: 15

Arg Phe Xaa Xaa Ser Xaa Asp Thr Ser Val Ser Thr Ala Tyr Leu Gln
1               5                   10                  15

Ile Ser Ser Leu Lys Ala Glu Asp Thr Ala Val Tyr Xaa Cys Xaa Arg
            20                  25                  30

<210> SEQ ID NO 16
<211> LENGTH: 11
<212> TYPE: PRT
<213> ORGANISM: Artificial sequence
<220> FEATURE:

```
<223> OTHER INFORMATION: Synthetic polypeptide

<400> SEQUENCE: 16

Trp Gly Gln Gly Thr Thr Val Thr Val Ser Ser
1               5                   10

<210> SEQ ID NO 17
<211> LENGTH: 734
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (22)..(22)
<223> OTHER INFORMATION: Xaa is Gln or Glu
<220> FEATURE:
<221> NAME/KEY: MISC_FEATURE
<222> LOCATION: (23)..(23)
<223> OTHER INFORMATION: Xaa is Val or Ile
<220> FEATURE:
<221> NAME/KEY: MISC_FEATURE
<222> LOCATION: (30)..(30)
<223> OTHER INFORMATION: Xaa is Ser or Pro
<220> FEATURE:
<221> NAME/KEY: MISC_FEATURE
<222> LOCATION: (67)..(67)
<223> OTHER INFORMATION: Xaa is Glu or Lys
<220> FEATURE:
<221> NAME/KEY: MISC_FEATURE
<222> LOCATION: (90)..(90)
<223> OTHER INFORMATION: Xaa is Val or Ala
<220> FEATURE:
<221> NAME/KEY: MISC_FEATURE
<222> LOCATION: (91)..(91)
<223> OTHER INFORMATION: Xaa is Phe or Leu
<220> FEATURE:
<221> NAME/KEY: MISC_FEATURE
<222> LOCATION: (93)..(93)
<223> OTHER INFORMATION: Xaa is Leu or Met
<220> FEATURE:
<221> NAME/KEY: MISC_FEATURE
<222> LOCATION: (116)..(116)
<223> OTHER INFORMATION: Xaa is Tyr or Phe
<220> FEATURE:
<221> NAME/KEY: MISC_FEATURE
<222> LOCATION: (118)..(118)
<223> OTHER INFORMATION: Xaa is Ala or Val
<220> FEATURE:
<221> NAME/KEY: MISC_FEATURE
<222> LOCATION: (514)..(514)
<223> OTHER INFORMATION: Xaa is Ile or Val
<220> FEATURE:
<221> NAME/KEY: MISC_FEATURE
<222> LOCATION: (604)..(604)
<223> OTHER INFORMATION: Xaa is Tyr or Phe

<400> SEQUENCE: 17

Gly Ser Met Glu Phe Gly Leu Ser Trp Leu Phe Leu Val Ala Ile Leu
1               5                   10                  15

Lys Gly Val Gln Cys Xaa Xaa Gln Leu Val Gln Ser Gly Xaa Glu Leu
            20                  25                  30

Lys Lys Pro Gly Ala Ser Val Lys Val Ser Cys Lys Ala Ser Gly Tyr
        35                  40                  45

Thr Phe Thr Asp Phe Ser Met Asn Trp Val Arg Gln Ala Pro Gly Gln
    50                  55                  60

Gly Leu Xaa Trp Met Gly Trp Ile Asn Thr Glu Thr Gly Glu Pro Thr
65                  70                  75                  80

Tyr Ala Asp Asp Phe Lys Gly Arg Phe Xaa Xaa Ser Xaa Asp Thr Ser
                85                  90                  95
```

```
Val Ser Thr Ala Tyr Leu Gln Ile Ser Ser Leu Lys Ala Glu Asp Thr
            100                 105                 110
Ala Val Tyr Xaa Cys Xaa Arg Ile Asp Tyr Trp Gly Gln Gly Thr Thr
            115                 120                 125
Val Thr Val Ser Ser Ala Ser Thr Lys Gly Pro Ser Val Phe Pro Leu
        130                 135                 140
Ala Pro Ser Ser Lys Ser Thr Ser Gly Gly Thr Ala Ala Leu Gly Cys
145                 150                 155                 160
Leu Val Lys Asp Tyr Phe Pro Glu Pro Val Thr Val Ser Trp Asn Ser
                165                 170                 175
Gly Ala Leu Thr Ser Gly Val His Thr Phe Pro Ala Val Leu Gln Ser
            180                 185                 190
Ser Gly Leu Tyr Ser Leu Ser Ser Val Val Thr Val Pro Ser Ser Ser
        195                 200                 205
Leu Gly Thr Gln Thr Tyr Ile Cys Asn Val Asn His Lys Pro Ser Asn
    210                 215                 220
Thr Lys Val Asp Lys Lys Val Glu Pro Lys Ser Cys Asp Lys Thr His
225                 230                 235                 240
Thr Cys Pro Pro Cys Pro Ala Pro Glu Leu Leu Gly Gly Pro Ser Val
                245                 250                 255
Phe Leu Phe Pro Pro Lys Pro Lys Asp Thr Leu Met Ile Ser Arg Thr
            260                 265                 270
Pro Glu Val Thr Cys Val Val Val Asp Val Ser His Glu Asp Pro Glu
        275                 280                 285
Val Lys Phe Asn Trp Tyr Val Asp Gly Val Glu Val His Asn Ala Lys
    290                 295                 300
Thr Lys Pro Arg Glu Glu Gln Tyr Asn Ser Thr Tyr Arg Val Val Ser
305                 310                 315                 320
Val Leu Thr Val Leu His Gln Asp Trp Leu Asn Gly Lys Glu Tyr Lys
                325                 330                 335
Cys Lys Val Ser Asn Lys Ala Leu Pro Ala Pro Ile Glu Lys Thr Ile
            340                 345                 350
Ser Lys Ala Lys Gly Gln Pro Arg Glu Pro Gln Val Tyr Thr Leu Pro
        355                 360                 365
Pro Ser Arg Asp Glu Leu Thr Lys Asn Gln Val Ser Leu Thr Cys Leu
    370                 375                 380
Val Lys Gly Phe Tyr Pro Ser Asp Ile Ala Val Glu Trp Glu Ser Asn
385                 390                 395                 400
Gly Gln Pro Glu Asn Asn Tyr Lys Thr Thr Pro Pro Val Leu Asp Ser
                405                 410                 415
Asp Gly Ser Phe Phe Leu Tyr Ser Lys Leu Thr Val Asp Lys Ser Arg
            420                 425                 430
Trp Gln Gln Gly Asn Val Phe Ser Cys Ser Val Met His Glu Ala Leu
        435                 440                 445
His Asn His Tyr Thr Gln Lys Ser Leu Ser Leu Ser Pro Gly Lys Arg
    450                 455                 460
Lys Arg Arg Ala Pro Val Lys Gln Thr Leu Asn Phe Asp Leu Leu Lys
465                 470                 475                 480
Leu Ala Gly Asp Val Glu Ser Asn Pro Gly Pro Asp Met Arg Val Pro
                485                 490                 495
Ala Gln Leu Leu Gly Leu Leu Leu Leu Trp Phe Pro Gly Ser Arg Cys
            500                 505                 510
Asp Xaa Val Met Thr Gln Ser Pro Leu Ser Leu Pro Val Thr Pro Gly
```

```
            515                 520                 525
Glu Pro Ala Ser Ile Ser Cys Arg Ser Ser Gln Ser Leu Val His Ser
530                 535                 540

Asn Gly Asn Thr Tyr Leu His Trp Tyr Leu Gln Lys Pro Gly Gln Ser
545                 550                 555                 560

Pro Gln Leu Leu Ile Tyr Lys Val Ser Asn Arg Phe Ser Gly Val Pro
                565                 570                 575

Asp Arg Phe Ser Gly Ser Gly Ser Gly Thr Asp Phe Thr Leu Lys Ile
            580                 585                 590

Ser Arg Val Glu Ala Glu Asp Val Gly Val Tyr Xaa Cys Phe Gln Ser
        595                 600                 605

Thr His Val Pro His Thr Phe Gly Gln Gly Thr Lys Leu Glu Ile Lys
    610                 615                 620

Arg Thr Val Ala Ala Pro Ser Val Phe Ile Phe Pro Pro Ser Asp Glu
625                 630                 635                 640

Gln Leu Lys Ser Gly Thr Ala Ser Val Val Cys Leu Leu Asn Asn Phe
                645                 650                 655

Tyr Pro Arg Glu Ala Lys Val Gln Trp Lys Val Asp Asn Ala Leu Gln
            660                 665                 670

Ser Gly Asn Ser Gln Glu Ser Val Thr Glu Gln Asp Ser Lys Asp Ser
        675                 680                 685

Thr Tyr Ser Leu Ser Ser Thr Leu Thr Leu Ser Lys Ala Asp Tyr Glu
    690                 695                 700

Lys His Lys Val Tyr Ala Cys Glu Val Thr His Gln Gly Leu Ser Ser
705                 710                 715                 720

Pro Val Thr Lys Ser Phe Asn Arg Gly Glu Cys Glx Leu Glu
                725                 730
```

```
<210> SEQ ID NO 18
<211> LENGTH: 442
<212> TYPE: PRT
<213> ORGANISM: Artificial sequence
<220> FEATURE:
<223> OTHER INFORMATION: Synthetic polypeptide

<400> SEQUENCE: 18

Glu Ile Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asp Phe
            20                  25                  30

Ser Met Asn Trp Val Arg Gln Ala Pro Gly Gln Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Leu Ser Met Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Val Arg Ile Asp Tyr Trp Gly Gln Gly Thr Thr Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
```

```
            145                 150                 155                 160
        Gly Val His Thr Phe Pro Ala Val Leu Gln Ser Ser Gly Leu Tyr Ser
                        165                 170                 175

Leu Ser Ser Val Val Thr Val Pro Ser Ser Ser Leu Gly Thr Gln Thr
                        180                 185                 190

Tyr Ile Cys Asn Val Asn His Lys Pro Ser Asn Thr Lys Val Asp Lys
                        195                 200                 205

Lys Val Glu Pro Lys Ser Cys Asp Lys Thr His Thr Cys Pro Pro Cys
            210                 215                 220

Pro Ala Pro Glu Leu Leu Gly Gly Pro Ser Val Phe Leu Phe Pro Pro
        225                 230                 235                 240

Lys Pro Lys Asp Thr Leu Met Ile Ser Arg Thr Pro Glu Val Thr Cys
                        245                 250                 255

Val Val Val Asp Val Ser His Glu Asp Pro Glu Val Lys Phe Asn Trp
                        260                 265                 270

Tyr Val Asp Gly Val Glu Val His Asn Ala Lys Thr Lys Pro Arg Glu
                        275                 280                 285

Glu Gln Tyr Asn Ser Thr Tyr Arg Val Val Ser Val Leu Thr Val Leu
            290                 295                 300

His Gln Asp Trp Leu Asn Gly Lys Glu Tyr Lys Cys Lys Val Ser Asn
        305                 310                 315                 320

Lys Ala Leu Pro Ala Pro Ile Glu Lys Thr Ile Ser Lys Ala Lys Gly
                        325                 330                 335

Gln Pro Arg Glu Pro Gln Val Tyr Thr Leu Pro Pro Ser Arg Asp Glu
                        340                 345                 350

Leu Thr Lys Asn Gln Val Ser Leu Thr Cys Leu Val Lys Gly Phe Tyr
                        355                 360                 365

Pro Ser Asp Ile Ala Val Glu Trp Glu Ser Asn Gly Gln Pro Glu Asn
            370                 375                 380

Asn Tyr Lys Thr Thr Pro Pro Val Leu Asp Ser Asp Gly Ser Phe Phe
        385                 390                 395                 400

Leu Tyr Ser Lys Leu Thr Val Asp Lys Ser Arg Trp Gln Gln Gly Asn
                        405                 410                 415

Val Phe Ser Cys Ser Val Met His Glu Ala Leu His Asn His Tyr Thr
                        420                 425                 430

Gln Lys Ser Leu Ser Leu Ser Pro Gly Lys
            435                 440

<210> SEQ ID NO 19
<211> LENGTH: 219
<212> TYPE: PRT
<213> ORGANISM: Artificial sequence
<220> FEATURE:
<223> OTHER INFORMATION: Synthetic polypeptide

<400> SEQUENCE: 19

Asp Ile Val Met Thr Gln Ser Pro Leu Ser Leu Pro Val Thr Pro Gly
        1               5                   10                  15

Glu Pro Ala Ser Ile Ser Cys Arg Ser Ser Gln Ser Leu Val His Ser
                        20                  25                  30

Asn Gly Asn Thr Tyr Leu His Trp Tyr Leu Gln Lys Pro Gly Gln Ser
                    35                  40                  45

Pro Gln Leu Leu Ile Tyr Lys Val Ser Asn Arg Phe Ser Gly Val Pro
                50                  55                  60

Asp Arg Phe Ser Gly Ser Gly Ser Gly Thr Asp Phe Thr Leu Lys Ile
```

```
                65                  70                  75                  80
        Ser Arg Val Glu Ala Glu Asp Val Gly Val Tyr Tyr Cys Phe Gln Ser
                            85                  90                  95

Thr His Val Pro His Thr Phe Gly Gln Gly Thr Lys Leu Glu Ile Lys
                           100                 105                 110

Arg Thr Val Ala Ala Pro Ser Val Phe Ile Phe Pro Pro Ser Asp Glu
                           115                 120                 125

Gln Leu Lys Ser Gly Thr Ala Ser Val Val Cys Leu Leu Asn Asn Phe
                130                 135                 140

Tyr Pro Arg Glu Ala Lys Val Gln Trp Lys Val Asp Asn Ala Leu Gln
        145                 150                 155                 160

Ser Gly Asn Ser Gln Glu Ser Val Thr Glu Gln Asp Ser Lys Asp Ser
                            165                 170                 175

Thr Tyr Ser Leu Ser Ser Thr Leu Thr Leu Ser Lys Ala Asp Tyr Glu
                            180                 185                 190

Lys His Lys Val Tyr Ala Cys Glu Val Thr His Gln Gly Leu Ser Ser
                            195                 200                 205

Pro Val Thr Lys Ser Phe Asn Arg Gly Glu Cys
                            210                 215

<210> SEQ ID NO 20
<211> LENGTH: 442
<212> TYPE: PRT
<213> ORGANISM: Artificial sequence
<220> FEATURE:
<223> OTHER INFORMATION: Synthetic polypeptide

<400> SEQUENCE: 20

Glu Ile Gln Leu Val Gln Ser Gly Ser Glu Leu Lys Lys Pro Gly Ala
        1               5                   10                  15

Ser Val Lys Val Ser Cys Lys Ala Ser Gly Tyr Thr Phe Thr Asp Phe
                        20                  25                  30

Ser Met Asn Trp Val Arg Gln Ala Pro Gly Gln Gly Leu Lys Trp Met
                    35                  40                  45

Gly Trp Ile Asn Thr Glu Thr Gly Glu Pro Thr Tyr Ala Asp Asp Phe
            50                  55                  60

Lys Gly Arg Phe Ala Leu Ser Met Asp Thr Ser Val Ser Thr Ala Tyr
        65                  70                  75                  80

Leu Gln Ile Ser Ser Leu Lys Ala Glu Asp Thr Ala Val Tyr Phe Cys
                        85                  90                  95

Val Arg Ile Asp Tyr Trp Gly Gln Gly Thr Thr Val Thr Val Ser Ser
                    100                 105                 110

Ala Ser Thr Lys Gly Pro Ser Val Phe Pro Leu Ala Pro Ser Ser Lys
                    115                 120                 125

Ser Thr Ser Gly Gly Thr Ala Ala Leu Gly Cys Leu Val Lys Asp Tyr
                130                 135                 140

Phe Pro Glu Pro Val Thr Val Ser Trp Asn Ser Gly Ala Leu Thr Ser
        145                 150                 155                 160

Gly Val His Thr Phe Pro Ala Val Leu Gln Ser Ser Gly Leu Tyr Ser
                            165                 170                 175

Leu Ser Ser Val Val Thr Val Pro Ser Ser Ser Leu Gly Thr Gln Thr
                            180                 185                 190

Tyr Ile Cys Asn Val Asn His Lys Pro Ser Asn Thr Lys Val Asp Lys
                            195                 200                 205

Lys Val Glu Pro Lys Ser Cys Asp Lys Thr His Thr Cys Pro Pro Cys
```

-continued

```
               210                 215                 220
Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 21
<211> LENGTH: 219
<212> TYPE: PRT
<213> ORGANISM: Artificial sequence
<220> FEATURE:
<223> OTHER INFORMATION: Synthetic polypeptide

<400> SEQUENCE: 21

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Phe Gln Ser
                85                  90                  95

Thr His Val Pro His Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
```

```
            130                 135                 140
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
            210                 215

<210> SEQ ID NO 22
<211> LENGTH: 442
<212> TYPE: PRT
<213> ORGANISM: Artificial sequence
<220> FEATURE:
<223> OTHER INFORMATION: Synthetic polypeptide

<400> SEQUENCE: 22

Glu Ile Gln Leu Val Gln Ser Gly Pro Glu Leu Lys Lys Pro Gly Ala
1               5                   10                  15

Ser Val Lys Val Ser Cys Lys Ala Ser Gly Tyr Thr Phe Thr Asp Phe
                20                  25                  30

Ser Met Asn Trp Val Arg Gln Ala Pro Gly Gln Gly Leu Lys Trp Met
            35                  40                  45

Gly Trp Ile Asn Thr Glu Thr Gly Glu Pro Thr Tyr Ala Asp Asp Phe
50                  55                  60

Lys Gly Arg Phe Ala Leu Ser Met Asp Thr Ser Val Ser Thr Ala Tyr
65                  70                  75                  80

Leu Gln Ile Ser Ser Leu Lys Ala Glu Asp Thr Ala Val Tyr Phe Cys
                85                  90                  95

Val Arg Ile Asp Tyr Trp Gly Gln Gly Thr Thr Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr Lys Val Asp Lys
        195                 200                 205

Lys Val Glu Pro Lys Ser Cys Asp Lys Thr His Thr Cys Pro Pro Cys
    210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
```

```
                    275                 280                 285
Glu Gln Tyr Asn Ser Thr Tyr Arg Val Val Ser Val Leu Thr Val Leu
290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 23
<211> LENGTH: 219
<212> TYPE: PRT
<213> ORGANISM: Artificial sequence
<220> FEATURE:
<223> OTHER INFORMATION: Synthetic polypeptide

<400> SEQUENCE: 23

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Phe Gln Ser
                85                  90                  95

Thr His Val Pro His Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
```

```
                195                 200                 205
Pro Val Thr Lys Ser Phe Asn Arg Gly Glu Cys
    210                 215
```

<210> SEQ ID NO 24
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 24
ggcgcagatc tattgacgtc aat                                           23

<210> SEQ ID NO 25
<211> LENGTH: 26
<212> TYPE: DNA
<213> ORGANISM: Artificial sequence
<220> FEATURE:
<223> OTHER INFORMATION: Synthetic polynucleotide

<400> SEQUENCE: 25
ggcaagctta attctttgcc aaaatg                                        26

<210> SEQ ID NO 26
<211> LENGTH: 25
<212> TYPE: DNA
<213> ORGANISM: Artificial sequence
<220> FEATURE:
<223> OTHER INFORMATION: Synthetic polynucleotide

<400> SEQUENCE: 26
aatcccggga cagctcaggg ctgcg                                         25

<210> SEQ ID NO 27
<211> LENGTH: 31
<212> TYPE: DNA
<213> ORGANISM: Artificial sequence
<220> FEATURE:
<223> OTHER INFORMATION: Synthetic polynucleotide

<400> SEQUENCE: 27
ggcggcgctt cgaaaaagcc agcaaaagct c                                  31

<210> SEQ ID NO 28
<211> LENGTH: 50
<212> TYPE: DNA
<213> ORGANISM: Artificial sequence
<220> FEATURE:
<223> OTHER INFORMATION: Synthetic polynucleotide

<400> SEQUENCE: 28
cagaagagcc tctccctgtc tccgggtaaa aggaagaggc gagcacctgt              50

<210> SEQ ID NO 29
<211> LENGTH: 49
<212> TYPE: DNA
<213> ORGANISM: Artificial sequence
<220> FEATURE:
<223> OTHER INFORMATION: Synthetic polynucleotide

<400> SEQUENCE: 29
gcccagcagc tgggcgggca cgcgcatgtc gggcccagga ttggactca               49